(12) United States Patent
Rockhold

(10) Patent No.: US 7,654,261 B1
(45) Date of Patent: Feb. 2, 2010

(54) AUTOMATED SYSTEM AND DEVICE FOR MANAGEMENT AND DISPENSATION OF RESPIRATORY THERAPY MEDICATIONS

(76) Inventor: Ann-Maree Rockhold, 1028 Malone St., Palm Bay, FL (US) 32907

( * ) Notice: Subject to any disclaimer, the term of this patent is extended or adjusted under 35 U.S.C. 154(b) by 645 days.

(21) Appl. No.: 11/390,561

(22) Filed: Mar. 28, 2006

Related U.S. Application Data

(60) Provisional application No. 60/666,225, filed on Mar. 29, 2005.

(51) Int. Cl.
*A61M 16/00* (2006.01)
*G06F 17/00* (2006.01)
*A61M 15/00* (2006.01)

(52) U.S. Cl. .............. 128/204.18; 128/202.27; 128/202.13; 128/204.21; 128/204.23; 700/237

(58) Field of Classification Search ............ 128/200.24, 128/202.13; 280/79.11, 79.2, 79.3; 700/231, 700/237, 240; 433/77
See application file for complete search history.

(56) References Cited

U.S. PATENT DOCUMENTS

| | | | |
|---|---|---|---|
| 3,744,672 A | 7/1973 | Dangles et al. ............... 221/82 |
| 3,762,601 A | 10/1973 | McLaughlin ................... 221/2 |
| 3,998,356 A | 12/1976 | Christensen ................... 221/2 |
| 4,113,098 A | 9/1978 | Howard ...................... 206/540 |
| 4,207,992 A | 6/1980 | Brown ......................... 221/15 |
| 4,267,942 A | 5/1981 | Wick, Jr. et al. ................ 221/2 |
| 4,504,153 A | 3/1985 | Schollmeyer et al. ......... 368/10 |
| 4,512,500 A | 4/1985 | Belbin, Sr. .................... 221/82 |
| D280,132 S | 8/1985 | McLaughlin ................ D24/31 |
| 4,572,403 A | 2/1986 | Benaroya ........................ 221/3 |
| 4,674,651 A | 6/1987 | Scidmore et al. ................ 221/3 |
| 4,695,954 A | 9/1987 | Rose et al. ................... 364/413 |
| 4,717,042 A | 1/1988 | McLaughlin ................... 221/3 |
| 4,747,514 A | 5/1988 | Stone ............................. 221/4 |
| 4,785,969 A | 11/1988 | McLaughlin ................... 221/2 |
| 4,811,764 A | 3/1989 | McLaughlin ................. 141/98 |
| 4,847,764 A | 7/1989 | Halvorson ................... 364/413 |
| 5,014,875 A | 5/1991 | McLaughlin et al. ........... 221/2 |
| 5,431,299 A | 7/1995 | Brewer et al. ................... 221/2 |
| 5,536,084 A | 7/1996 | Curtis et al. ........... 364/413.01 |
| RE35,743 E | 3/1998 | Pearson ......................... 221/2 |
| 6,175,779 B1 | 1/2001 | Barrett ....................... 700/242 |
| 6,339,732 B1 * | 1/2002 | Phoon et al. ................ 700/237 |

(Continued)

*Primary Examiner*—Justine R Yu
*Assistant Examiner*—Clinton Ostrup
(74) *Attorney, Agent, or Firm*—Brian S. Steinberger; Joyce P. Morlin; Law Offices of Brian S. Steinberger, P.A.

(57) ABSTRACT

A computerized, mobile respiratory therapy medication dispensing device, apparatus, system, and method having a mobile housing having a plurality of different size drawers for storing and transporting respiratory therapy medication, devices, and supplies. The housing mounted on a plurality of wheels has a biometric sensor, such as a magnetic badge reader for security, a pulse oximeter mounted in the cabinet for patient monitoring, a computer system mounted on the cabinet including a central processing unit, a transmitter and receiver system responsive to the central processing unit for transmitting and receiving data, the transmitter and receiver system capable of transmitting and receiving data through radio frequency signals, a display responsive to the central processing unit for displaying data, and an input device for inputting data into the computer system, and a rechargeable energy source.

13 Claims, 16 Drawing Sheets

U.S. PATENT DOCUMENTS

| | | | |
|---|---|---|---|
| 6,493,220 B1 * | 12/2002 | Clark et al. | 361/686 |
| 6,655,545 B1 * | 12/2003 | Sonneborn | 221/7 |
| 6,996,455 B2 | 2/2006 | Eggenberger et al. | 700/231 |
| 7,314,164 B2 * | 1/2008 | Bonalle et al. | 235/380 |
| 2002/0095238 A1 * | 7/2002 | Ahlin et al. | 700/243 |
| 2002/0183976 A1 * | 12/2002 | Pearce | 702/188 |
| 2003/0120384 A1 | 6/2003 | Haitin et al. | 700/242 |
| 2004/0054436 A1 | 3/2004 | Haitin et al. | 700/236 |
| 2004/0186357 A1 * | 9/2004 | Soderberg et al. | 600/300 |
| 2005/0159784 A1 * | 7/2005 | Arceta | 607/20 |

* cited by examiner

PATIENT: Marie Collins         MR#: 1111111111    ADM. DATE: 7/11/06
    DX: Bronchitis

TX GIVEN   TX NOT GIVEN   MEDICATION:      GIVEN VIA:    HR:___ ___ ___

BBS:          CLEAR        DIMINISHED       FINE COARSE       INSPIRATORY
              EXPIRATORY              RALES       WHEEZES
     RHONCHI

LOBE:                       RUL   LUL   RML   LLL   RLL

COUGH:    NONE  PRODUCTIVE  NON-PRODUCTIVE   LOOSE        TIGHT
     DRY
           HACKING     PAROXYSMAL       WEAK         MODERATE
     STRONG

SPUTUM:   NONE        SCANT       SMALL      MODERATE
     COPIOUS
           CLEAR      WHITE       PALE YELLOW      YELLOW       GREEN
           TAN        RUST        RED        THICK        THIN
           TENACIOUS

FIG. 13

AUTOMATED SYSTEM AND DEVICE FOR MANAGEMENT AND DISPENSATION OF RESPIRATORY THERAPY MEDICATIONS

This invention claims the benefit of priority from U.S. Provisional Application Ser. No. 60/666,225 filed Mar. 29, 2005.

FIELD OF THE INVENTION

This invention relates generally to pharmaceutical management and dispensing systems, and more specifically to an automated system, apparatus, device and method for management and dispensation of inhaled pulmonary medications as administered by a respiratory therapist under the direct orders of a physician.

BACKGROUND AND PRIOR ART

Interest in the use of information technology and automation to address the management and dispensation of medication safely, without errors, timely and effectively has never been greater. Healthcare organizations and healthcare professionals are in agreement that medication error represents one of the most pervasive, preventable, and costly sources of patient harm.

Various devices are known, such as, a timed apparatus for dispensing medicines in U.S. Pat. No. 3,762,601 to McLaughlin, U.S. Pat. No. 4,207,992 to Brown, U.S. Pat. No. 4,572,403 and an electronic system for dispensing items (U.S. Pat. No. 3,998,356 to Christensen) and medications (U.S. Pat. No. 4,747,514 to Stone). A mechanical pill-dispensing and storage container is disclosed in U.S. Pat. No. 3,744,672 to Dangles et al., U.S. Pat. No. 4,113,098 to Howard, U.S. Pat. No. 4,512,500 to Belbin, Sr., U.S. Pat. No. 4,674,651 to Scidmore et al.

Pharmaceutical dispensing cabinets with recording systems and automatic accountability of items are disclosed in U.S. Pat. No. 4,267,942 to Wick, Jr. et al., U.S. Pat. No. 4,504,153 to Schollmeyer et al. and a computer controlled system for dispensing drugs in a health care institution is discussed in U.S. Pat. No. 4,847,764 to Halvorson.

Further innovations include a modular medication dispensing system with a microprocessor or portable memory device as disclosed in U.S. Pat. No. 4,695,954 to Rose et al. and U.S. Pat. No. 4,717,042 to McLaughlin. Improved variations of a medication dispensing system are provided by McLaughlin in Design Patent 280,132, U.S. Pat. No. 4,785,969 and U.S. Pat. No. 4,811,764 designed to dispense a variety of different medications.

Beginning in the early 1990s, the use of programmable systems (computers) for controlled access storage of medication and other pharmaceuticals in a medical facility became the state of the art as disclosed in U.S. Pat. No. 5,014,875 to McLaughlin et al., U.S. Pat. No. 5,431,299 to Brewer et al., U.S. Pat. No. 5,536,084 to Curtis et al., Reissue Patent Re. 35,743 to Pearson and U.S. Pat. No. 6,996,455 B2 to Eggenberger et al.

Most recently, specialized carts have been developed such as the computerized unit dose medication dispensing cart of Barrett in U.S. Pat. No. 6,175,779 B1 and point of care medication dispensation as shown in U.S. Patent Publication 2004/0054436 A1 to Haitin et al. and U.S. Patent Publication 2003/0120384 A1 to Haitin et al.

Thus, we find an approximately 50-year history of automated or mechanical medication dispensing systems. Systems that are centralized in medical facilities, decentralized in various treatment units and finally, point of care medication dispensing carts.

Centralized medication dispensation systems offer the advantage of a single, centralized inventory and a lower overall inventory and the disadvantages of large size, high cost, expenditure of high-cost professional time to stock and retrieve medication, and reliance on efficient delivery systems.

Decentralized, medical unit medication dispensation systems are smaller size and lower cost relative to the centrally-located devices and provide more immediate access to medications and automated documentation of medication administration with the primary disadvantage of reliance on efficient delivery systems.

Point of care systems, as described in the two U.S. Patent Publications 2003/0120384 A1 and 2004/0054435 A1 to Haitin et al., are designed to enable immediate exchange of patient data at the bedside. However, these devices are generally limited to measuring vital signs such as temperature, pulse rate and blood pressure. Collectively, the above references do not provide a point of care, respiratory therapy medication dispensing system. Further, none of the above references provide a point of care, respiratory therapy medication dispensing system capable of collecting respiratory data simultaneously with medication dispensing. Respiratory data includes measurements of, sensing or observation of such conditions as, respiratory rates, $SpO_2$ (oxygen levels in the blood), heart rate, lung sounds, respiratory distress, work of breathing, amount and consistency of sputum production, skin color, temperature and whether or not the patient is diaphoretic (clammy, sweating).

As a further development, in 2005, the Joint Commission on Accreditation of Hospital Organizations (JCAHO) established new Patient Safety Standards that requires that all prescribed medications be dispensed to the management/dispenser systems by the hospital pharmacy. The new Patient Safety Standards by the JCAHO will reduce unwanted drug interactions and repeat dosing of similar medications by passing all prescriptions, including pulmonary prescriptions, under the watchful eye of hospital pharmacy staff. The plan is for all respiratory therapy medications to be stocked in "medication rooms" on the nursing floors into the same devices, either centralized or decentralized units, that nursing staff have been using for years.

The advantages of "medication rooms" are highlighted above in the discussion of centralized and decentralized medication dispensing units and are considered an affordable patient safety investment. The disadvantages of medication rooms include, but are not limited to, reliance on an efficient delivery system, the hectic day-to-day traffic in and out of the room by health practitioners.

In practice, shift change in the medication rooms is comparable to rush hour traffic as lines form at the dispensing system cabinet. Medication rooms are typically small and quickly become crowded with staff that are either waiting their turn at the dispensers or are preparing medications for administration to patients. In this crowded room, the risk of sharps injuries to staff is increased along with an increased risk of staff members' medications becoming mixed up with those of another staff member for lack of space.

Prior to 2005 and the implementation of the new Patient Safety Standards by the JCAHO (Joint Commission on Accreditation of Hospital Organizations), respiratory therapists maintained a private stock of inhaled medications in a medication room in the respiratory care department. Each respiratory therapist had his or her own system for organization of medication types kept in the many pockets of his or her uniform. This system which is no longer permitted under the new Patient Safety Standards, carried the risk of medication errors, but allowed for expedited delivery of patient care.

Patients are at increased risk for deterioration of their pulmonary status if a stat medication is required and the respiratory therapist has to stand in line for the patient's rescue medication. Other times patients will miss scheduled pulmonary medications because they are transferred off of the treatment floor for diagnostic tests while the therapist is in line in the medication room.

A further drawback in the medication room dispensation system for pulmonary or respiratory medications is that there is no standard method for storage and dispensation of metered dose inhalers (MDIs) that is practiced the same in all medical facilities. Frequently MDIs are stored in the medication rooms in patient-specific boxes. In some hospitals, there is some confusion as to whether nursing or respiratory therapists administer these medications which can result in double-dosing.

Still further, the medication room dispensation can result in loss of metered dose inhalers (MDIs) by respiratory and nursing staff. This results in the need for the medication to be re-dispensed by the pharmacy and the patient is re-charged for these expensive drugs. When the patient becomes aware that the charge has been made twice for an expensive medication through no fault of the patient, the hospital will be called and the charge must be removed from the bill; causing a loss of hospital revenues and personnel productivity.

If, respiratory therapy medications are the most recent addition to the dispensing systems, it is most likely that these medications will be stored in the bottom-most drawers requiring the therapist to repeatedly bend down to retrieve dispensed medications leading to an increased risk for back and knee injuries for the therapists.

Thus, it becomes apparent that there is a need for a system for the dispensation of respiratory medication designed to function within the new Patient Safety Standards; a system that moves with the therapist as they move through the hospital or medical facility administering inhaled pulmonary medication and various modalities of respiratory care. A system is needed that is designed to avoid knee and back injuries to therapists, the queuing and long waits for medications secured in centralized or decentralized units.

Thus, the need exists for solutions to the problems with the prior art.

SUMMARY OF THE INVENTION

The first objective of the present invention is to provide a mobile respiratory therapy medication dispensing system, apparatus, device and method.

The second objective of the present invention is to provide a tool, apparatus, device and method for dispensation of respiratory medications.

The third objective of the present invention is to provide a mobile respiratory therapy medication dispensing system, apparatus, device and method that allows monitoring of patient respiratory data, such as, respiratory rate, oxygen levels in the blood, and other conditions, during drug administration.

The fourth objective of the present invention is to provide a secure, mobile respiratory therapy station.

The fifth objective of the present invention is to provide an ergonomic device, system, apparatus and method to assist respiratory therapists to work more effectively.

The sixth objective of the present invention is to provide a mobile respiratory therapy medication dispensing system, apparatus, device and method that interfaces with hospital pharmacies to provide a direct record of drug dispensation by respiratory therapists.

The seventh objective of the present invention is to provide a mobile respiratory therapy medication dispensing system, apparatus, device and method that facilitates the tracking and stocking of respiratory medications by pharmacy personnel.

The eighth objective of the present invention is to provide a mobile respiratory therapy medication dispensing system, apparatus, device and method that expedites patient treatment and care.

The ninth objective of the present invention is to provide a mobile respiratory therapy medication dispensing system, apparatus, device and method that provides respiratory therapists with a portable device for charting patient care.

The tenth objective of the present invention is to provide a mobile respiratory therapy medication dispensing system, apparatus, device and method that controls and secures respiratory medications.

The eleventh objective of the present invention is to provide a mobile respiratory therapy medication dispensing system, apparatus, device and method that provides an automated dispensing system for trained and licensed professionals.

The twelfth objective of the present invention is to provide a mobile respiratory therapy medication dispensing system, apparatus, device and method that ensures that medications removed from the automated system have a matching physicians's order, in accordance with Federal, State and hospital guidelines, such as the new Patient Safety Standards by the Joint Commission on Accreditation of Hospital Organizations (JCAHO).

The novel invention eliminates knee and back injuries to therapists, and the queuing and long waits for medications secured in centralized or decentralized units that exist with prior art devices and techniques.

The device and medication dispensing system, apparatus, device and method of the present invention overcomes deficiencies in prior practices and provides for the first time a customized unit for respiratory therapists that dispense prepackaged unit dose pulmonary medications, bottles of mucolytic medication, metered dose inhalers (MDIs) and the like, as prescribed for a patient by a physician and authorized by a pharmacist. The present invention further assures safety through positive therapist identification, positive patient identification, medication verification at the patient's bedside, while respiratory data are being monitored and recorded in real time.

The preferred embodiment of a respiratory therapy cart includes a mobile cart having a housing with a plurality of wheels for making the housing mobile, a plurality of different size storage compartments in the housing for storing patient medications and supplies, a plurality of respiratory sensors attached to the housing for sensing respiratory conditions of patients in real time, a central processing unit in the housing for recording respiratory sensed parameters of a patient in real time, and a rechargeable energy source adjacent to the housing for providing power to the sensors and the central processing unit.

It is preferred that the mobile cart have six wheels, each being swivel and that the plurality of different size storage compartments, include one size for patient medications, and a different size for individual respiratory equipment. A separate wire basket is also a preferred compartment stored in the bottom portion of the cart.

It is preferred that a compartment with the one size for patient medications is for different inhaled pulmonary medications. The different inhaled pulmonary medications include bronchodilators, corticosteroids, inhaled antibiotics and mucolytics.

The respiratory sensors included in the mobile respiratory therapy cart are a pulse oximeter, a spirometer and an arterial blood gas analyzer, more preferably a pulse oximeter.

The preferred central processing unit for recording is a wireless laptop computer adapted to be operated by a respiratory therapist.

The preferred parameters that are sensed and recorded are respiratory rates, oxygen levels in the blood, heart rate, lung sounds, respiratory distress, amount and consistency of sputum production, skin color, temperature and diaphoretic condition of the patient.

The preferred renewable energy source for the respiratory therapy medication cart is a battery pack that is electrically recharged.

A preferred method for treating respiratory therapy patients with a mobile cart includes providing a mobile medication cart having a central processing unit with a plurality of respiratory sensors, biometric access validation scanner and respiratory therapy medication dispensers all powered by a rechargeable energy source, scanning biometric information of a respiratory therapist with the validation scanner in order to access the CPU and the respiratory therapy medication and allow for the cart to be become mobile, wheeling the mobile cart to a patient's bed after validation of the respiratory therapist biometric information, sensing respiratory conditions of the patient with the respiratory sensors, entering the sensed respiratory conditions of the patient into the central processing unit, dispensing respiratory therapy medications from the cart based on the sensed respiratory conditions, entering the medications dispensed to patient into the central processing unit, recharging the energy source, and returning the cart for restocking and stocking of respiratory therapy medication.

The preferred scanning of biometric information is from a magnetic identification (ID) badge on the respiratory therapist with a magnetic scanner, wherein the validation automatically activates power on the cart and non-validation deactivates the power to the cart.

The preferred wheels for wheeling of the medication cart includes six swivel wheels on the cart.

It is also preferred to sense the respiratory conditions of a patient by built-in respiratory equipment, hand-held equipment and manual input by the respiratory therapist.

The preferred respiratory equipment for sensing is a pulse oximeter, a spirometer or an arterial blood gas analyzer, more preferably a pulse oximeter.

The respiratory conditions of the patient sensed, recorded and entered into archives include respiratory rate, oxygen levels in the blood, heart rate, lung sounds, work of breathing, amount and consistency of sputum production, skin color, temperature and diaphoretic condition. The respiratory data are used to determine patient care and medications that will be dispensed. The preferred treatment is dispensing an inhaled pulmonary medication, wherein the inhaled pulmonary medication is at least one of a fast-acting bronchodilator, a less-fast acting bronchodilator, a corticosteroid, an inhaled antibiotic, and a mucolytic.

It is also preferred that medication be dispensed to a patient, based on sensed conditions, by a respiratory therapist and be recorded by manual in-put by the respiratory therapist.

Further objects and advantages of this invention will be apparent from the following detailed description of a presently preferred embodiment, which is illustrated in the accompanying flow charts and drawings.

BRIEF DESCRIPTION OF THE FIGURES

FIG. 13 is an exemplary illustration of a frame of the diagnostic program which illustrates the patient' respiratory information monitored in accordance with a preferred embodiment.

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the mobile respiratory therapy medication dispensing device of the present invention and method of using the same.

"Cart" "cabinet" "device" and "station" are used interchangeably herein when referring to the mobile unit for managing and dispensing respiration therapy medications.

"Compartment" and "Drawer" is used to include any type of box like storage unit that is made to slide in and out of a housing.

"Pulmonary" is used to mean relating to or affecting the lungs.

"Pulse oximeter" is a device that determines the oxygen saturation of the blood on an anesthetized patient using a sensor attached to a finger, yields a computerized read out, and sounds an alarm if the blood saturation becomes less than optimal.

"Respiratory" means of, relating to, used in, or affecting respiration or breathing, including respiratory organs, nerves and the like.

"Spirometer" is an instrument for measuring the volume of air entering and leaving the lungs as in inhaling or exhaling, respectively.

"$SpO_2$" is blood oxygen saturation measured by a pulse oximeter in percentage.

"Vital signs" are signs of life, including pulse rate, body temperature, respiratory rate and often, blood pressure of a person.

The circuitry for opening and closing drawers in the mobile respiratory therapy medication dispensing device of the present invention is described in U.S. Pat. No. 6,175,779 B1 to Barrett and U.S. Pat. No. 6,996,455 B2 to Eggenberger et al.; the teachings of which are incorporated herein by reference.

The basic components of the mobile respiratory therapy medication dispensing device or cart of the present invention, include, but are not limited to, a housing having a plurality of wheels, a plurality of different size storage compartments in the housing for storing patient medications, built-in respiratory sensors in the housing for sensing respiratory conditions, a respiratory sensor recorder, a processor having a memory (computer), a display screen, a communication medium for input and output of data, a staff identification scanning device to avoid any unauthorized use of the dispensing cart or station and a power source.

Figure 1:
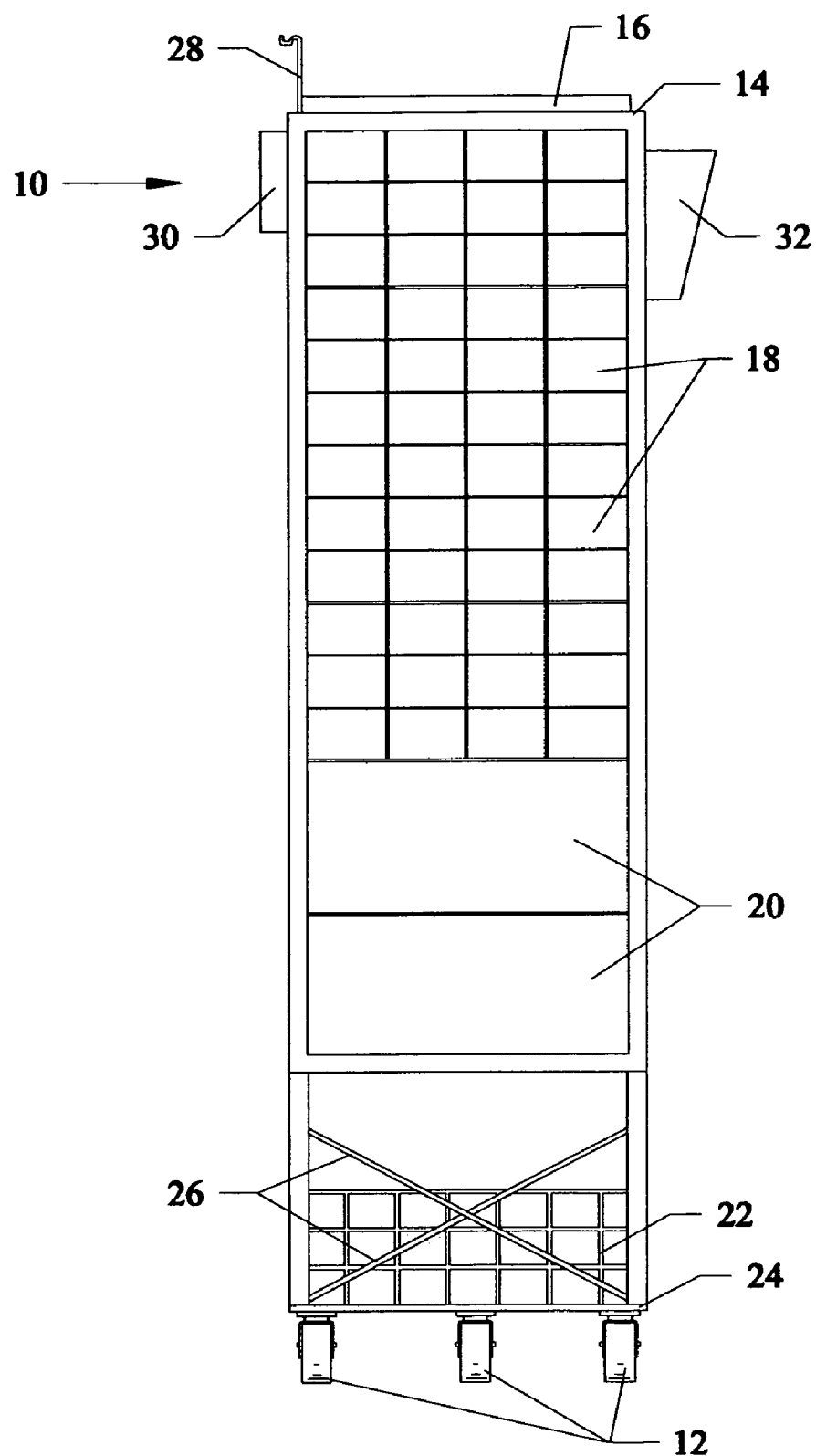
FIG. 1 is a front view of the mobile respiratory therapy medication dispensing device of the present invention.

FIG. 1 provides a front view of the preferred embodiment of the respiratory therapy medication dispensing cart of the present invention. The overall dimensions of cart 10 are approximately 35.56 centimeters (cm) (14 inches) wide by approximately 30.48 cm (12 inches) deep by approximately 127.0 cm (50 inches) in height (14"W×12"D×50"H). The height of the cart 10 is measured from the bottom of the swivel wheels 12 to the outer edge of the recessed area 14 supporting a wireless laptop computer 16. There are forty-eight medication drawers 18 for secure storage of each patient's inhaled pulmonary medications, each drawer measures approximately 5.08 cm (2 inches) wide×7.62 cm (3 inches) deep× 5.08 cm (2 inches) high (2"W×3"D×2"H).

Two larger drawers 20 provide secure storage of prescribed metered dose inhalers (MDIs), unit doses of saline, MDI spacers (Single-patient use devices to enhance MDI medication deposition in the lungs) turbohalers and disc inhalers (MDIs containing powdered medication which is not released under pressure like the traditional MDI that releases a "cloud" of medication to be inhaled), peak-flow meters (devices a patient blows into to measure the severity of bronchospasm), and the like. The large drawers 20 each measure approximately 30.48 cm (12 inches) wide by approximately 25.40 cm (10 inches) deep by approximately 15.24 cm (6 inches) in height (12"W×10"D×6"H).

A wire basket 22 is placed below the larger drawers 20 in a rack formed by the bottom 24 of the cart 10 and cross braces 26 that support and provide structural integrity to the side walls of the cart.

A hook 28 for hanging treatment bags is attached to and protrudes from the top of the cart 10. Hook 28 is a place for hanging equipment and other items so that the therapists's hands are free. A scanner 30 used for therapist identification and turning on the power to the cart protrudes from the left side of cart 10. An angled receptacle 32 for holding small devices, such as oxygen nipples, connectors and adaptors, protrudes from the right side of cart 10.

The wire basket 22, hook 28, and receptacle 32 are convenient design features that keep the therapist on the floor and maximize the therapist's availability for patient care.

Figure 2A:
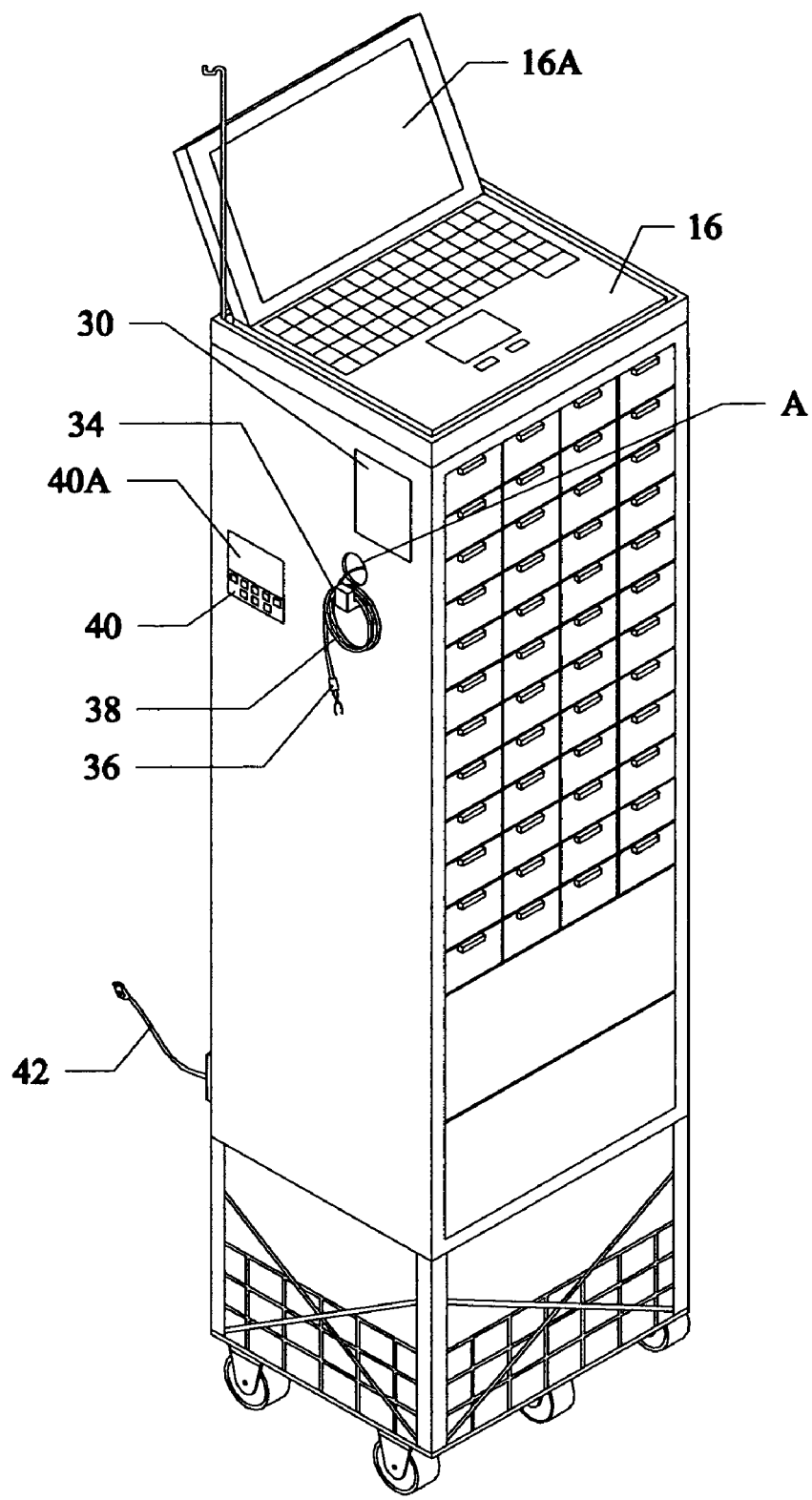
FIG. 2A is a perspective plan view of the mobile respiratory therapy medication dispensing device of the present invention.

FIG. 2A shows a perspective plan view of the mobile respiratory therapy medication dispensing device wherein the positioning of the wireless laptop computer 16 with display screen 16A is shown in greater detail. The therapist identification scanning device 30 is position in the top right corner of the left side wall, just above a hook 34 for hanging the pulse oximeter probe 36 with an approximately ten foot retractable cord 38, that is retractable into orifice A. The pulse oximeter 40 is recessed in the left side wall and has a display screen 40A for displaying $SpO_2$ data taken before, after or during the dispensing of medication. A power cord 42 provides and supports the power source for the unit.

Figure 2B:
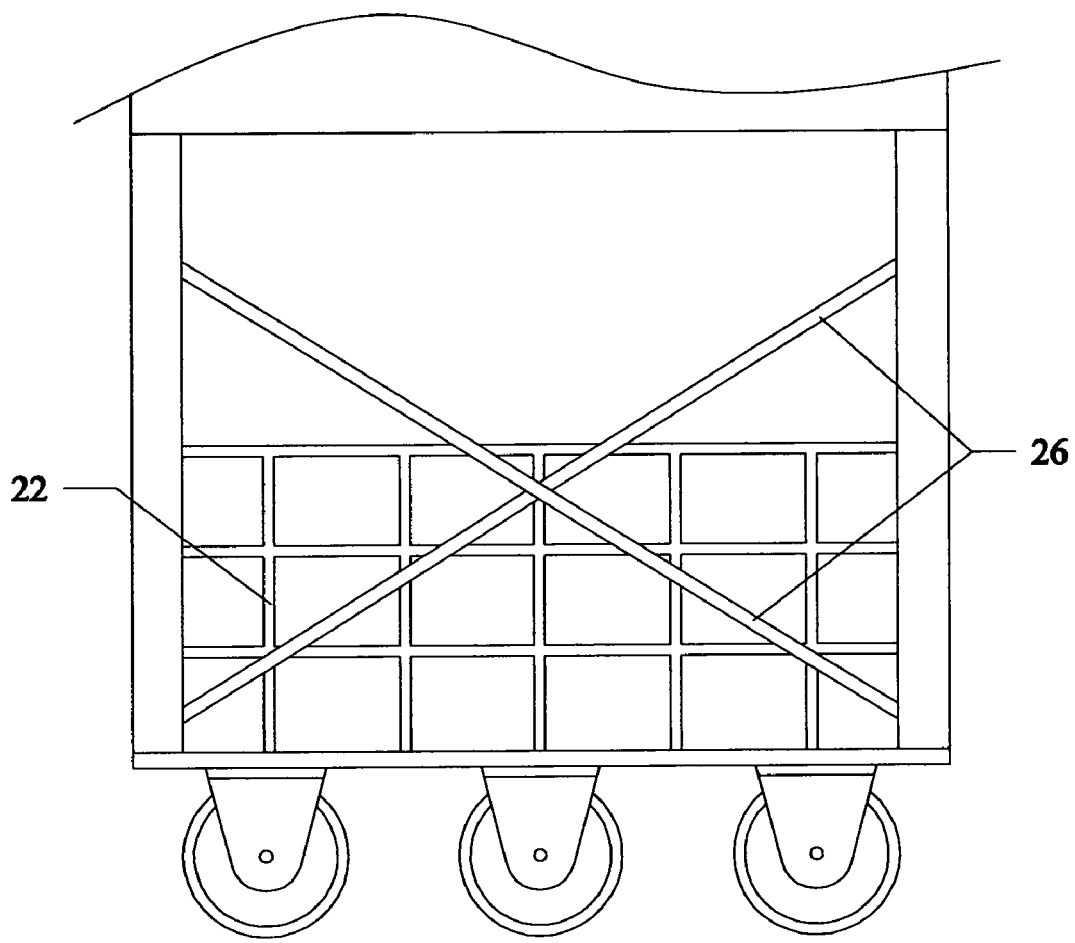
FIG. 2B is a front view of the bottom section of the mobile respiratory therapy medication dispensing device of the present invention showing the leg support and wire basket contained therein.

FIG. 2B is an enlarged view of the structural support and cross braces 26 which are also used to contain the wire basket 22. The wire basket 22 is used to carry extra supplies that may be required during a work shift, such as nebulizers, aerosol masks, oxygen administration devices (nasal cannulas, venturi masks, nonrebreather masks), flowmeters, arterial blood gas kits, and the like.

Figure 3A:
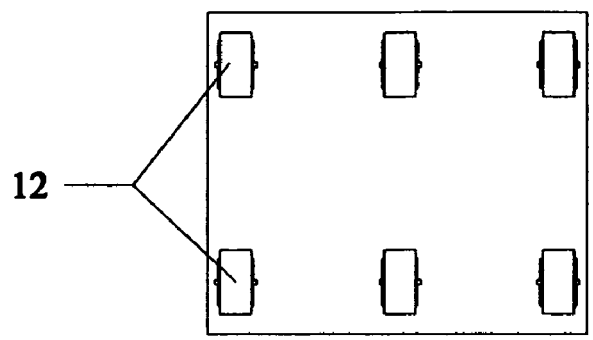
FIG. 3A is a bottom view of the mobile respiratory therapy medication dispensing device of the present invention showing six swivel wheels.

FIG. 3A is a bottom view of the computerized mobile respiratory therapy medication dispensing cart showing six swivel wheels 12 arranged to provide the most stable support for the cart. Two opposing wheels at the left and right side of the cart 10 would preferably have a locking mechanism to prevent the cart from pivoting or moving when it is necessary for the cart to remain in a fixed position. Swivel wheels with a locking feature are well known in the art and are available from Carpin Manufacturing, Inc., 411 Austin Road, Waterbury, Conn. 06705 or from Service Caster Corporation in West Reading, Pa 19611. The preferred wheels 12 for cart 10 are approximately 4 to 5 inches in diameter. With the arrangement of wheels 12, as shown in FIG. 3A, the cart is easily moved from room to room, and can be positioned in close proximity to the patient's bedside, as the therapist treats each patient.

Figure 3B:
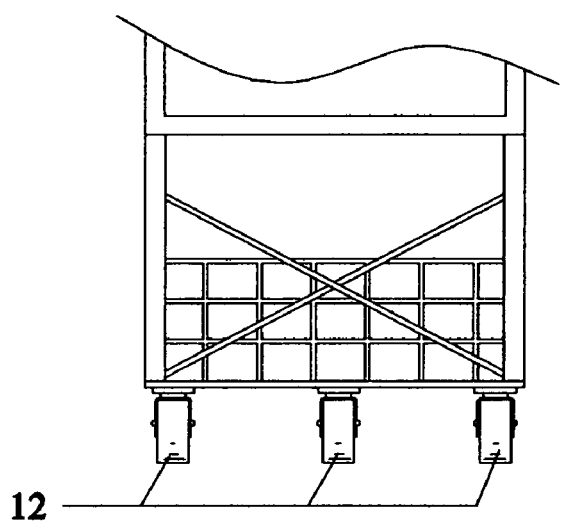
FIG. 3B is a front view of the bottom section of the mobile respiratory therapy medication dispensing device of the present invention showing the wheels in alignment and facing forward.
Figure 3C:
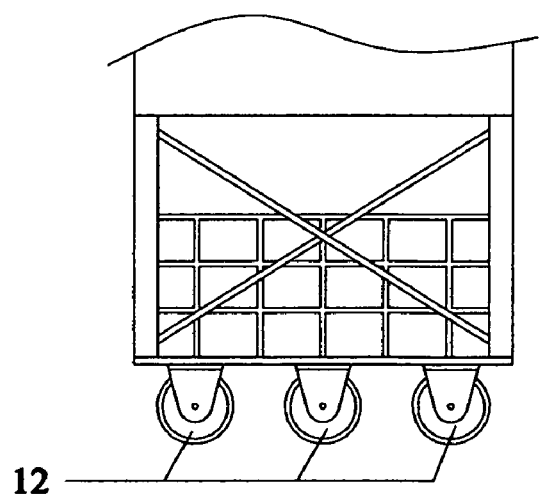
FIG. 3C is a front view of the bottom section of the mobile respiratory therapy medication dispensing device of the present invention showing the wheels in alignment and facing in a horizontal direction.

FIG. 3B shows the swivel wheels 12 facing forward in a front view of the bottom of cart 10. FIG. 3C shows the swivel wheels 12 facing horizontally in a front view of the bottom of the cart 10; thus the combination of FIGS. 3B and 3C show the swivel feature of the wheels 12.

Figure 4:
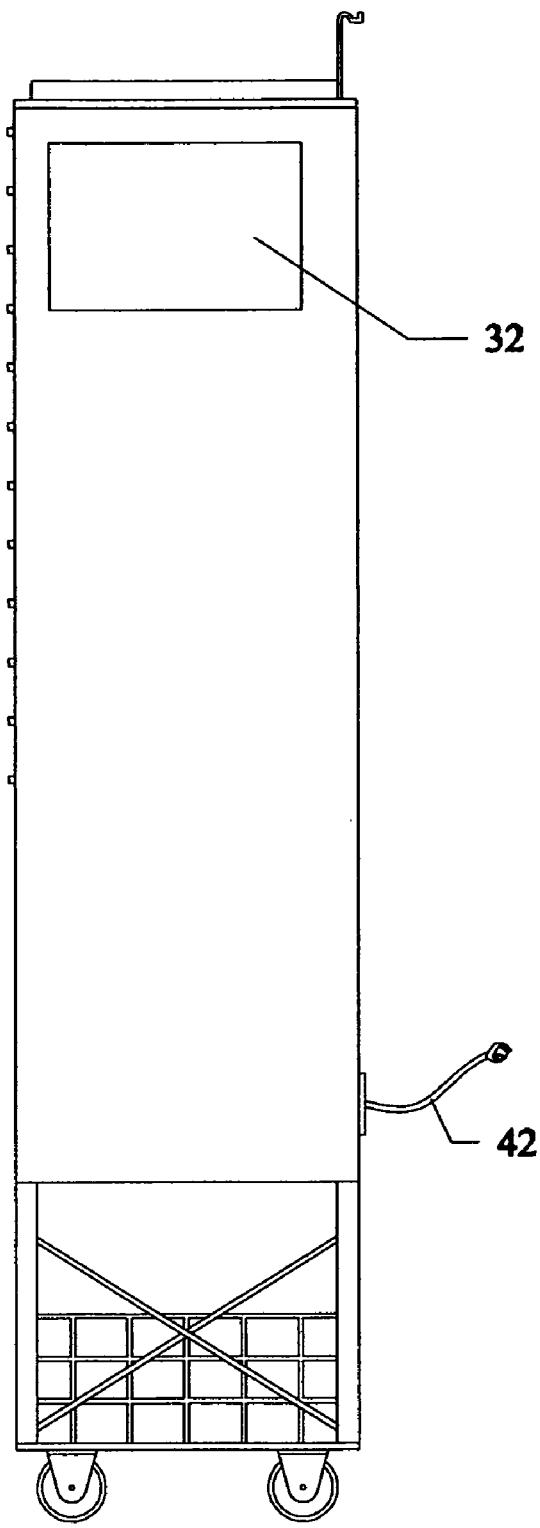
FIG. 4 is a right side view of the mobile respiratory therapy medication dispensing device of the present invention.

FIG. 4 is a right side view of cart 10 showing the position of a receptacle 32 for smaller devices like oxygen nipples, connectors and adaptors. Also shown in the power cord 42 which is used to charge batteries that are used to power the unit for up to 2 hours, so that the therapist can move freely through the hospital to provide point of care respiratory therapy for patients.

Figure 5:
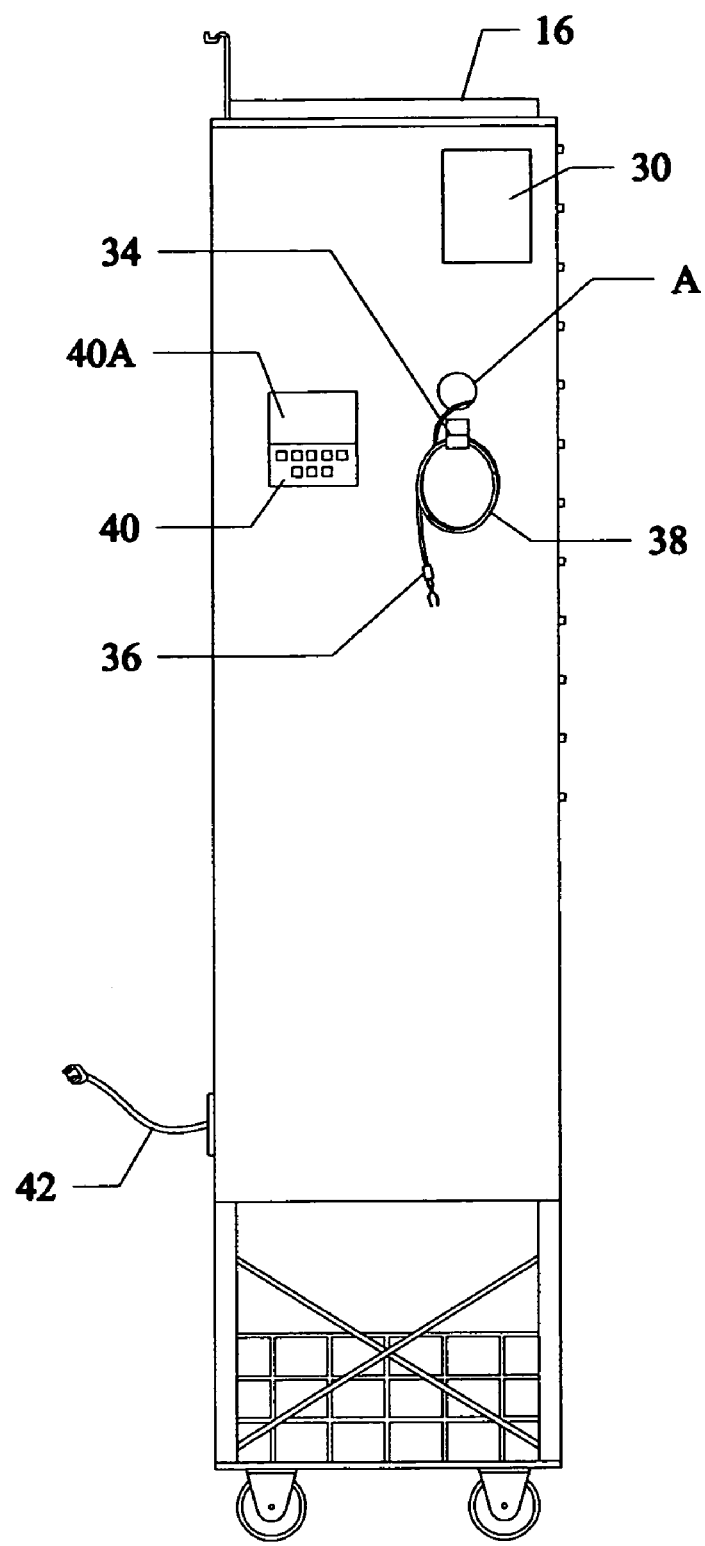
FIG. 5 is a left side view of the mobile respiratory therapy medication dispensing device of the present invention.

FIG. 5 is a left side view of the cart 10 showing the instrumentation and attachments discussed in FIG. 2A, namely, a badge scanner 30, a hook 34 for hanging the pulse oximeter probe 36 with an approximately ten foot retractable cord 38 and a pulse oximeter 40 recessed in the left side wall with a display screen 40A for displaying $SpO_2$ data.

Figure 6:
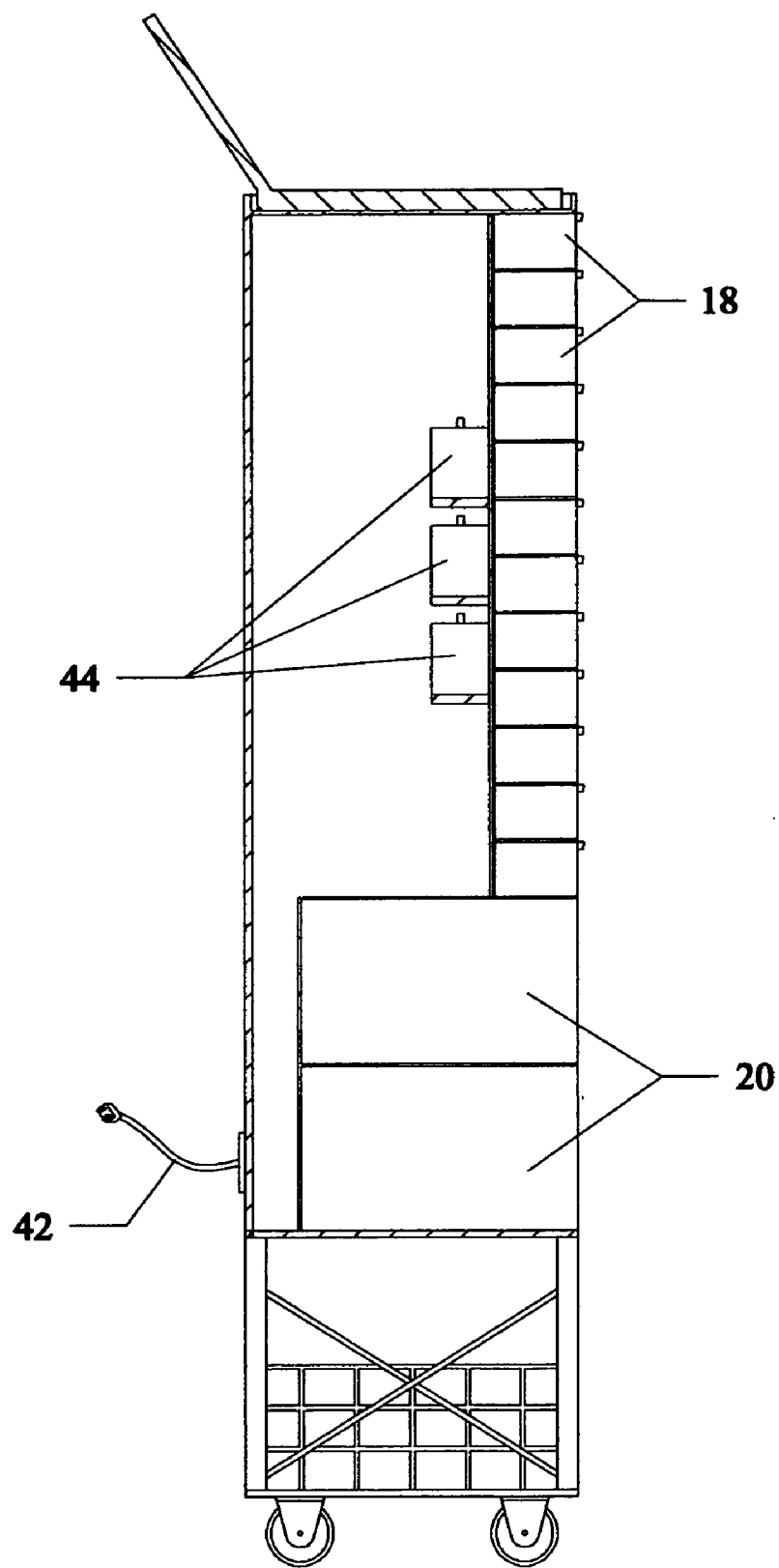
FIG. 6 is a cross-sectional view of the mobile respiratory therapy medication dispensing device of the present invention.

FIG. 6 is a cross-sectional view of cart 10 from front to back showing the location of battery packs 44 positioned behind the 48 unit drawers 18 and above the two larger drawers 20. The battery pack 44 is connected to power source 42 for recharging.

Figure 7:
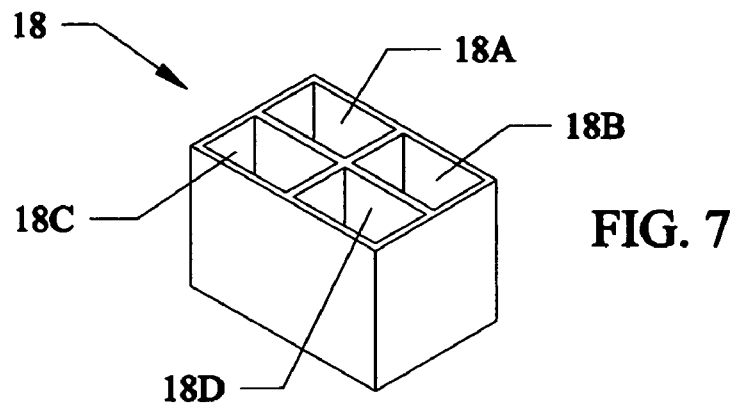
FIG. 7 is a perspective view of one of the small drawer compartments of the mobile respiratory therapy medication dispensing device of the present invention.

FIG. 7 provides detail of the smaller size drawer 18 for patient specific medication. Four separate compartments 18A, 18B, 18C, 18D are used to separate the various inhaled pulmonary medication classes, such as, but not limited to, bronchodilators, fast-acting and less-fact acting; corticosteroids; inhaled antibiotics; and mucolytics.

Separation of the drugs into the various classes is an added precaution taken to prevent medication errors, especially because the respiratory therapy medications usually are packaged in single-use vials and look very much alike.

Class 1 drugs, such as bronchodilators, are used to increase airway diameter to allow deeper, regular breathing in patients with pulmonary diseases that cause airway constriction and thus, difficulty breathing; they come in clear, single-use vials.

Class 2 drugs, such as corticosteroids, are stabilizers of lung function when they are inhaled. They decrease inflammation in the airways. The most common one comes in a different shaped, although a clear, single dose vial, it can be differentiated from the others based on the shape.

Class 3 drugs, such as inhaled antibiotics, are not frequently used, but common in specific patient populations, such as those with cystic fibrosis. It is a local antibiotic that is inhaled using a nebulizer and it also comes in a clear single-use vial.

Class 4 drugs, such as, mucolytics are inhaled drugs that break-down the chemical bonds in the mucus in the lungs, making them thinner and therefore easier to cough up and clear out pneumonias and the like. Some mucolytics come in clear single-use vials while other drugs in this class must be drawn out by syringe.

In FIG. 7 the four separate compartments are shown in a permanent configuration, which is the preferred arrangement. The well-defined separation of respiratory therapy drug classes, discussed above, is a very important step towards eliminating medication errors. A patient identification sticker (not shown) can be placed inside to minimize drawer confusion.

Figure 8:
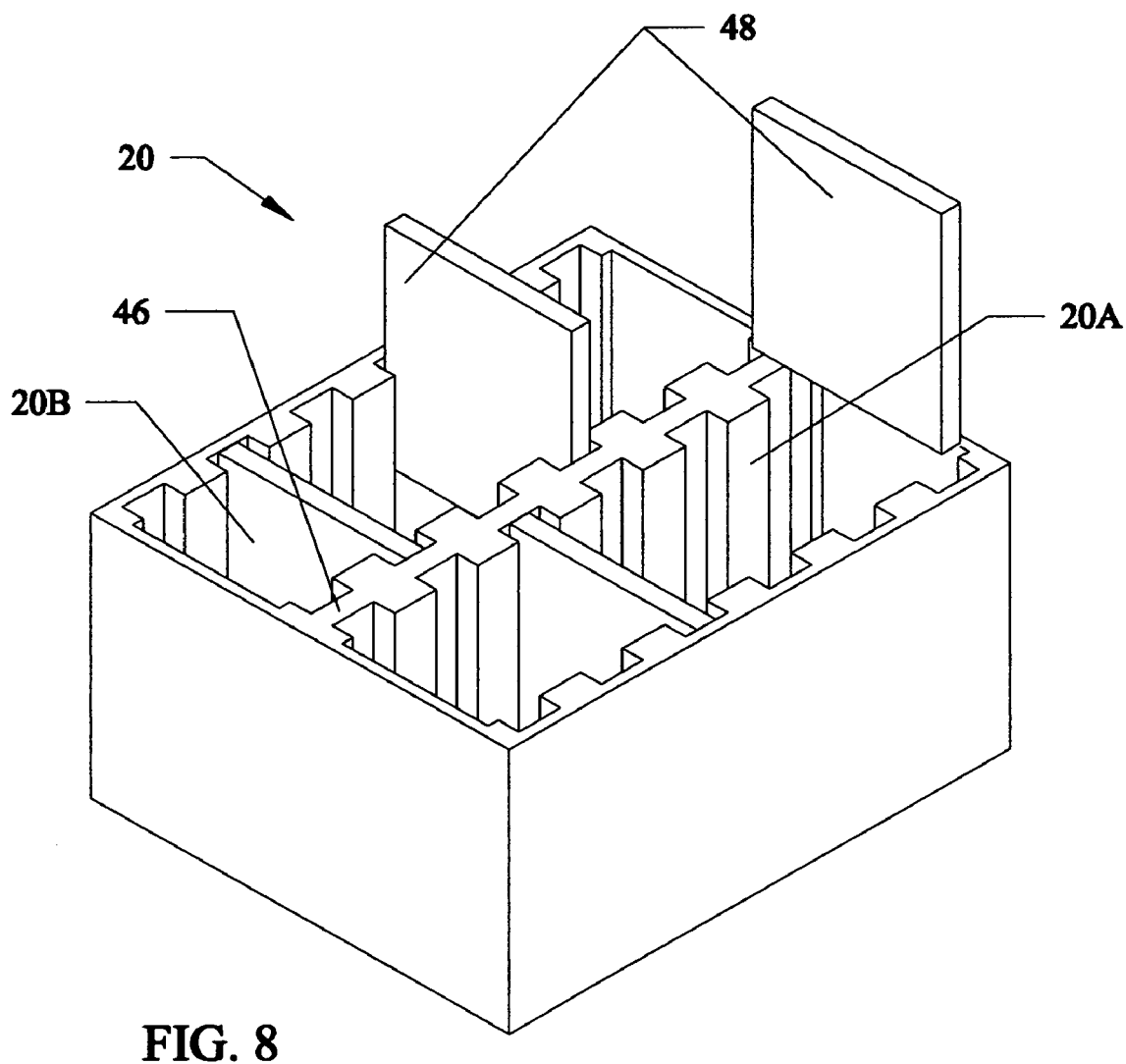
FIG. 8 is a perspective view of one of the larger drawer compartments of the mobile respiratory therapy medication dispensing device of the present invention.

FIG. 8 shows the inside of the larger drawer 20 which is permanently divided down the center 46 and further illustrates moveable dividers 48 used to create patient specific compartments, such as, 20A, 20B inside the larger drawer 20. Patient-specific compartment, such as 20A and 20B are used to securely store metered dose inhalers (MDIs), spacers, turbohalers, disc inhalers, peak flow meters, and the like. MDIs are different shapes and therefore are packaged in differently shaped and sized boxes. A common problem is loss; another is confusion about who is administering them, nurses or respiratory therapists?

Frequently, a patient will have nebulizer treatments and MDIs or even, multiple MDIs. The moveable dividers 48 shown in FIG. 8, create patient-specific compartments in the larger drawers 20. The adjustable compartments permit all of one patient's MDIs to be stored in one compartment identified by a patient identification sticker, as with the smaller drawers 18. The multiple compartments can also store the MDIs of a number of patients. This arrangement eliminates the loss of MDIs as well as any confusion about who is administering them. MDI loss costs hospital pharmacies a considerable amount each year, some MDIs cost $300.00 (2006 pricing) and when one is lost and a patient is recharged for a medication that the patient was not responsible for losing, the hospital has to bear the cost of a replacement.

Figure 9:
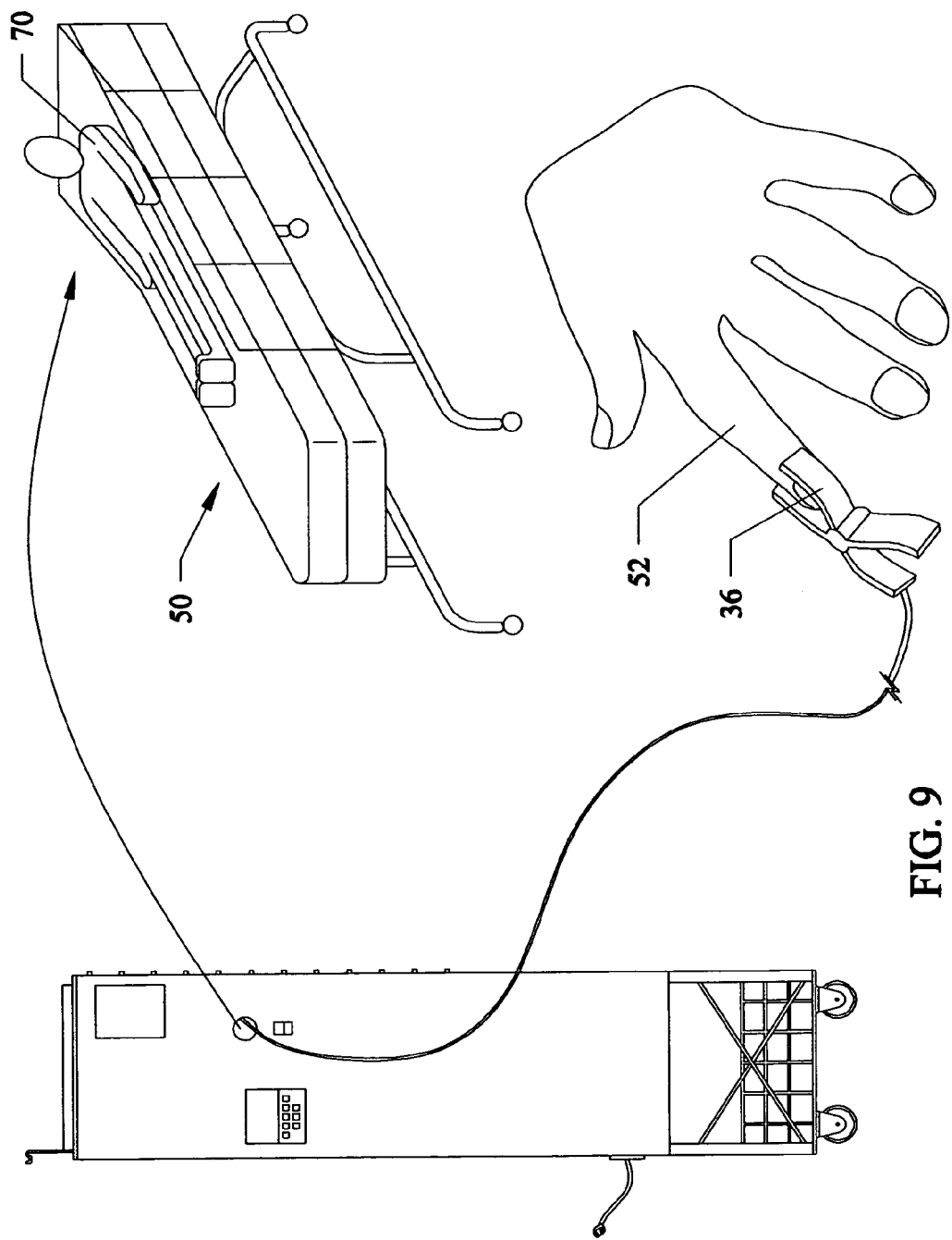
FIG. 9 is a schematic illustration of the use of the mobile respiratory therapy medication dispensing device of the present invention with a built-in pulse oximeter, at a patient's bedside with a pulse oximeter probe attached to the patient's finger.

FIG. 9 is a schematic layout of the mobile cart 10 of the present invention in close proximity to a patient's bed 50 and a close-up sketch of a pulse oximeter probe 36 on the patient's finger 52 at the patient's bedside. The patient is 70.

Figure 10:
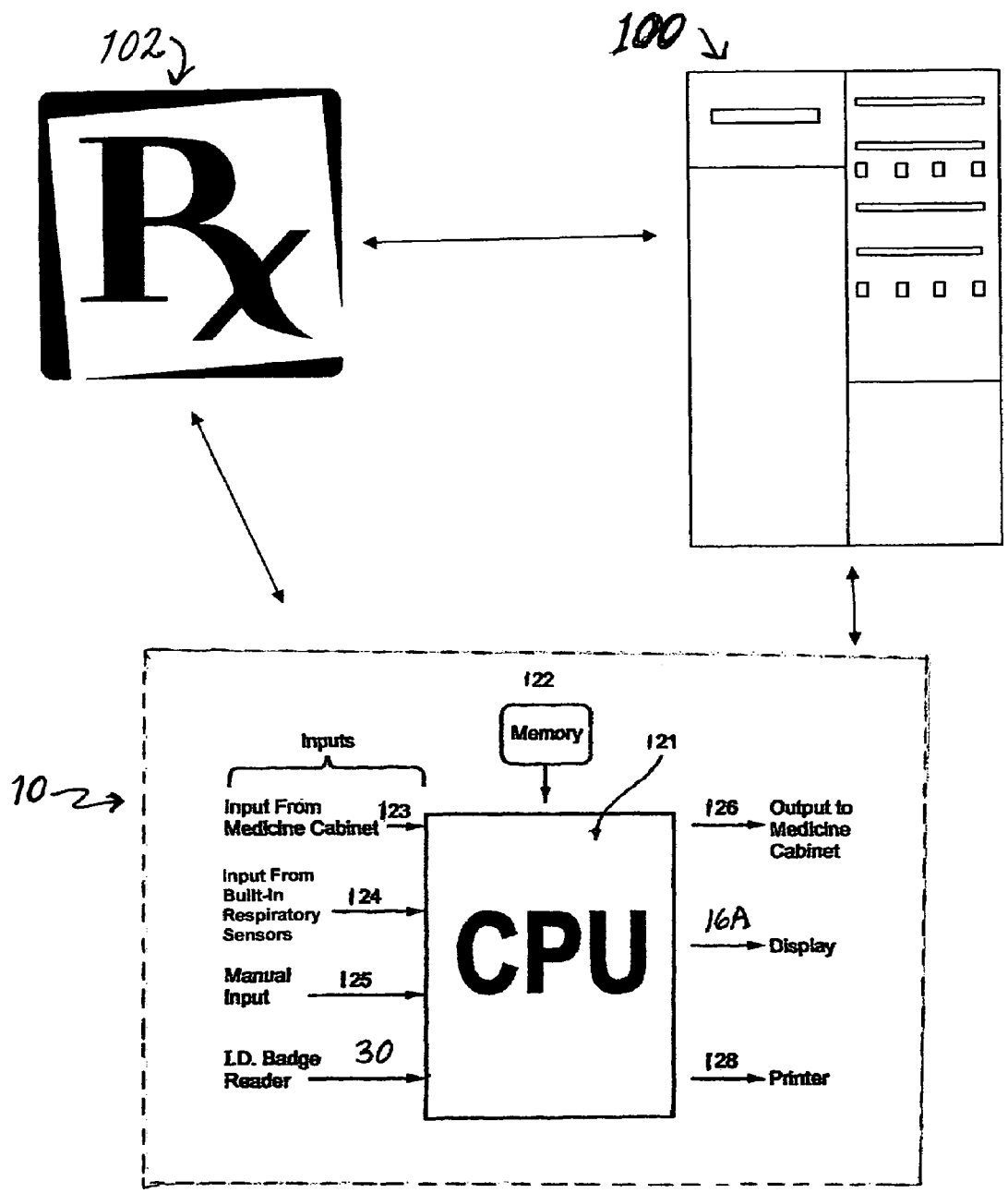
FIG. 10 is a block diagram illustrating the communication links between the various components of a preferred embodiment of a respiratory therapy medication dispensing system of the present invention.

In FIG. 10, the block diagram illustrates the communication links between the hospital archive 100 which contains patient information, pharmacy 102, and the mobile respiratory therapy medication dispenser cart 10. The medication therapy dispensing cart 10 employs a central processing unit (CPU) 121 with memory 122 and transmitting and receiving capabilities to recognize the therapist with the I.D. badge reader 30, then permit the respiratory therapist access to patient results in hospital archives 100, in order to help direct the respiratory plan of care.

The CPU 121 further allows the therapist to chart patient care at bedside, with input from built-in respiratory sensors 124 and manual in-put 125 of auditory and visual observations made by the therapist. The CPU 121 also provides the pharmacy 102 with a record of the dispensation and stock of medications in the computerized mobile respiratory therapy cart 10; this record is created from input from the medicine cabinet 123 and output to the medicine cabinet 126. At the end of each twelve hour shift, inhaled pulmonary medications are stocked or restocked by pharmacy staff.

The CPU 121 can download information to a printer or can include a printer 128 and a display screen 16A, which in alternative embodiments (not shown), the traditional laptop computer is replaced with a touch screen device.

Figure 11:
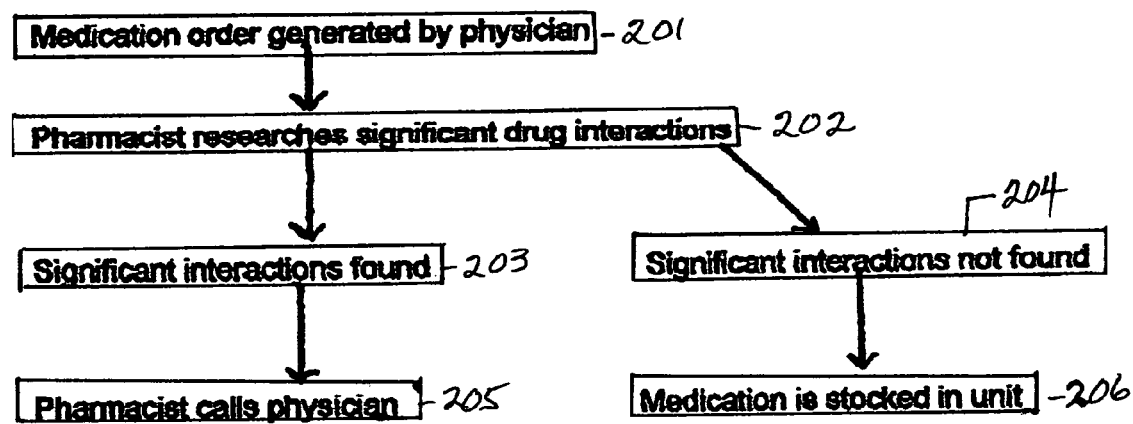
FIG. 11 is a flow chart of the interaction of physician and pharmacist with the mobile respiratory therapy medication dispensing device of the present invention.

FIG. 11 is a flow chart with steps numbered 201 to 206, showing that the medication order is generated by a physician to the pharmacist who researches to see if significant drug interactions are involved for the patient. If significant drug interactions are found, the pharmacist calls the physician to explore other possible medications. If no significant interactions are found, the medication is stocked in the respiratory therapy medication dispensing cart 10.

Figure 12:
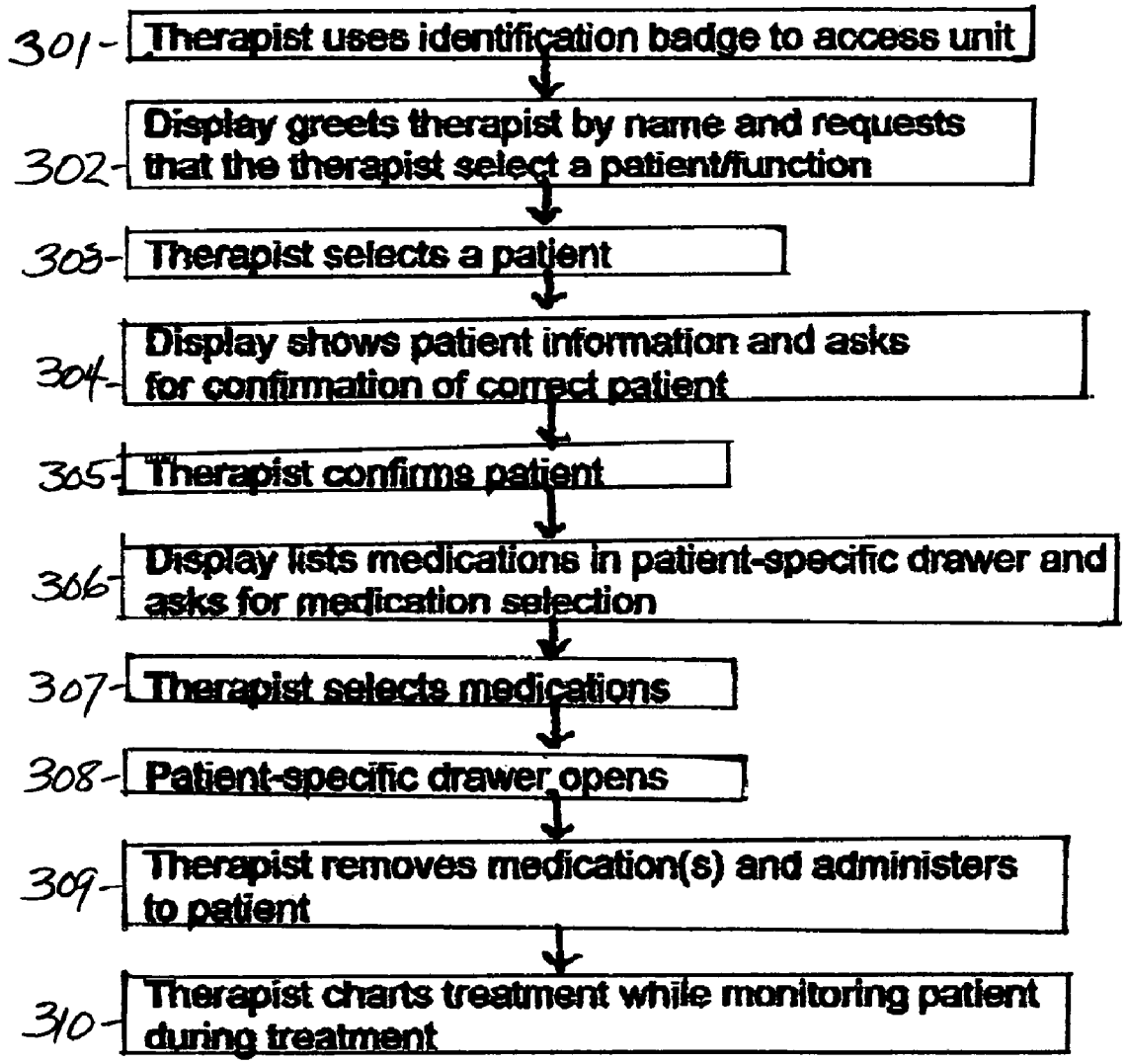
FIG. 12 is a flow chart of actions taken by a respiratory therapist using and interacting with the mobile respiratory therapy medication dispensing device of the present invention.

FIG. 12 is a flow chart with steps numbered 301 to 310, showing how the therapist operates the medication dispensing cart 10. First, the therapist uses a personal identification badge to access the unit. Cart 10 is shown with a magnetic identification badge-reader 30 for security, so that no unauthorized use is allowed, thus securing the medications in the respiratory therapy station. In an alternative embodiment, the badge scanner can be replaced with any biometric identification device, such as those distributed by UPEK, Inc. 2200 Powell Street, Suite 300, Emeryville, Calif. 94608. Validation of biometrics can also include, but is not limited to facial feature recognition, eye and retinal scan recognition, fingerprint validation, and the like, and combinations thereof.

After the respiratory therapist scans a personal ID badge that is recognized by the scanner, the power to the cart is automatically turned on with an electronic signal. The display screen 16A on the computer 16 presents a list of patients to choose from. The therapist selects a patient; the display screen 16A shows patient information and asks for confirmation of correct patient.

After the therapist confirms that the patient selection is correct, a display screen appears listing that particular patient's inhaled pulmonary medications in a patient-specific drawer 18 and asks the therapist for medication selection. The therapist selects the medications and the patient-specific drawer 18 opens in response to an electronic signal allowing the therapist to access the specific patient's medication. The therapist removes medication(s) when the patient's specific drawer 18 opens and administers the medication to patient (FIG. 10, 70). If the patient is receiving metered dose inhalers (MDIs), the therapist can select them from the screen and the larger drawer 20 where the inhalers are stored will open in response to an electronic signal, as well.

With the computerized portable respiratory therapy cart at the patient's bedside, the therapist places the pulse oximeter probe 36 on the patient's finger and bends over to listen to the lungs. While listening to the patient's lung sounds, the patient's respiratory condition can be observed on the pulse oximeter display 40A. The therapist administers the treatment and uses the computer 16 to chart/access diagnostic results by inputting data into the computer 16 while monitoring the respiratory data of patient at the bedside. The lightweight, approximately 100 pounds, computerized mobile, respiratory therapy medication dispensing cart is moved easily from room to room as the therapist treats each patient.

The process outlined above is repeated for each patient receiving respiratory care on each scheduled treatment round, typically, every four hours. At the end of each treatment round, the cart plugs into a standard electrical outlet to recharge the batteries for the next round.

FIG. 13 is an exemplary illustration of patient respiratory information selections that can be displayed on screen 16A. The respiratory therapist chooses from these selections in charting a patients treatment and inputting the information into the hospital archives (FIG. 10, 100).

Figure 14:
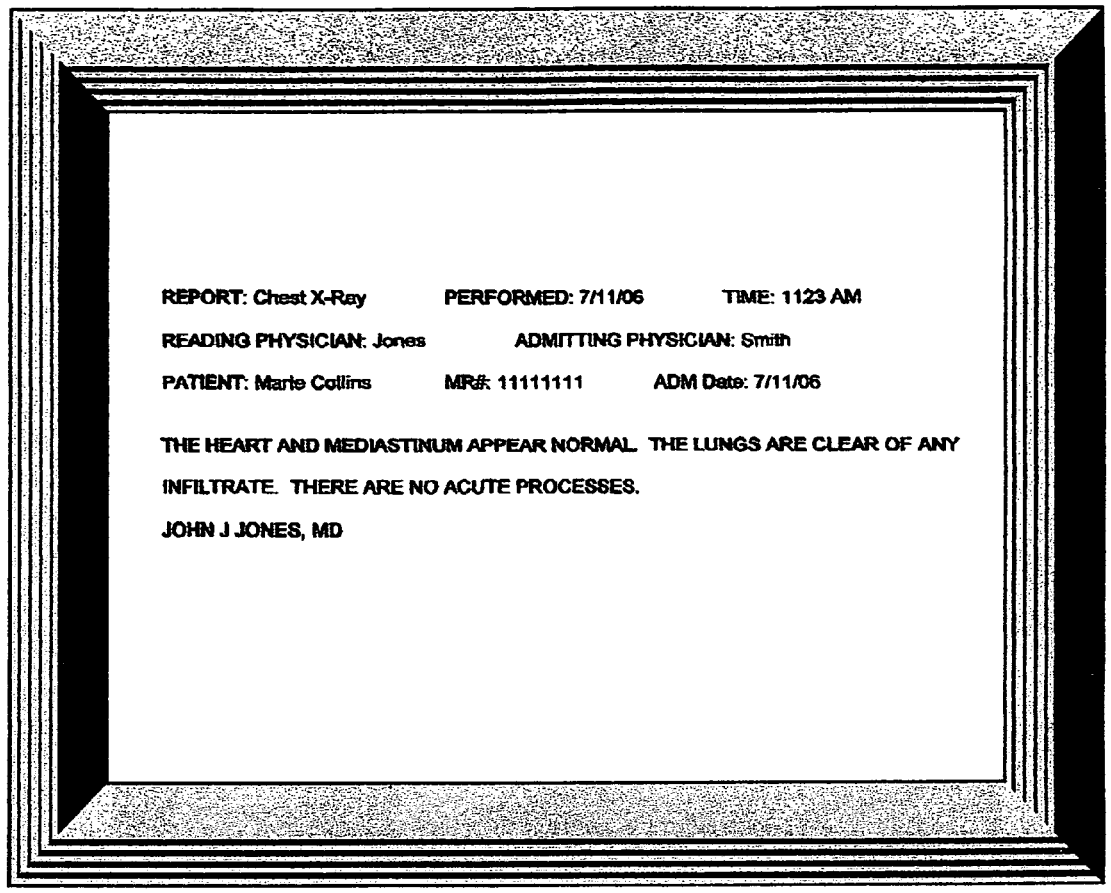
FIG. 14 is an exemplary illustration of a frame of patient information available for display re: Chest X-ray for a respiratory therapist using the mobile respiratory therapy medication dispensing device of the present invention.

FIG. 14 is an exemplary illustration of patient respiratory information that can be displayed on screen 16A when the therapist accesses information from a chest X-ray obtained from hospital archives (FIG. 10, 100).

Figure 15:
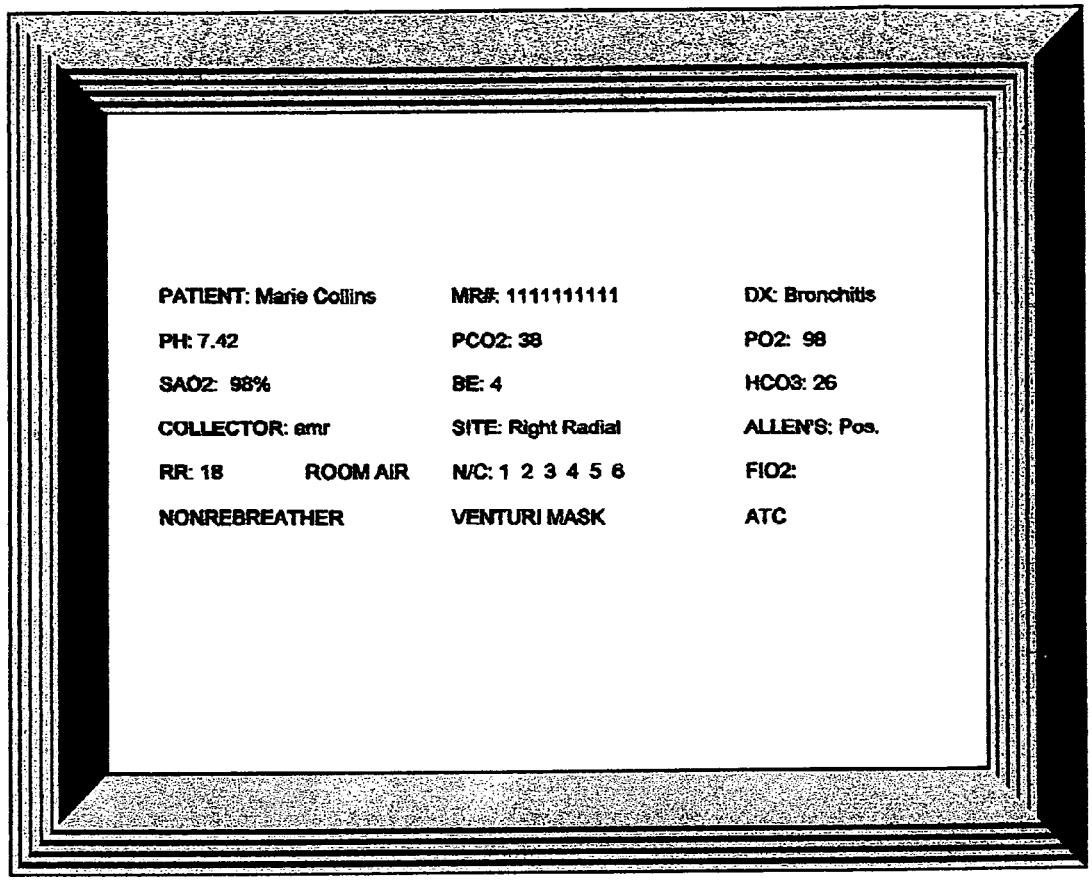
FIG. 15 is an exemplary illustration of a frame of patient information available for display re: an arterial blood gas result obtained by a respiratory therapist and entered into the patient's archive using the mobile respiratory therapy medication dispensing device of the present invention.

FIG. 15 is an exemplary illustration of arterial blood gas (ABG) result accessed from the hospital archive that can be displayed on screen 16A. A respiratory therapist performed the test and placed the result in the archive. Abnormal results direct patient care.

Figure 16:
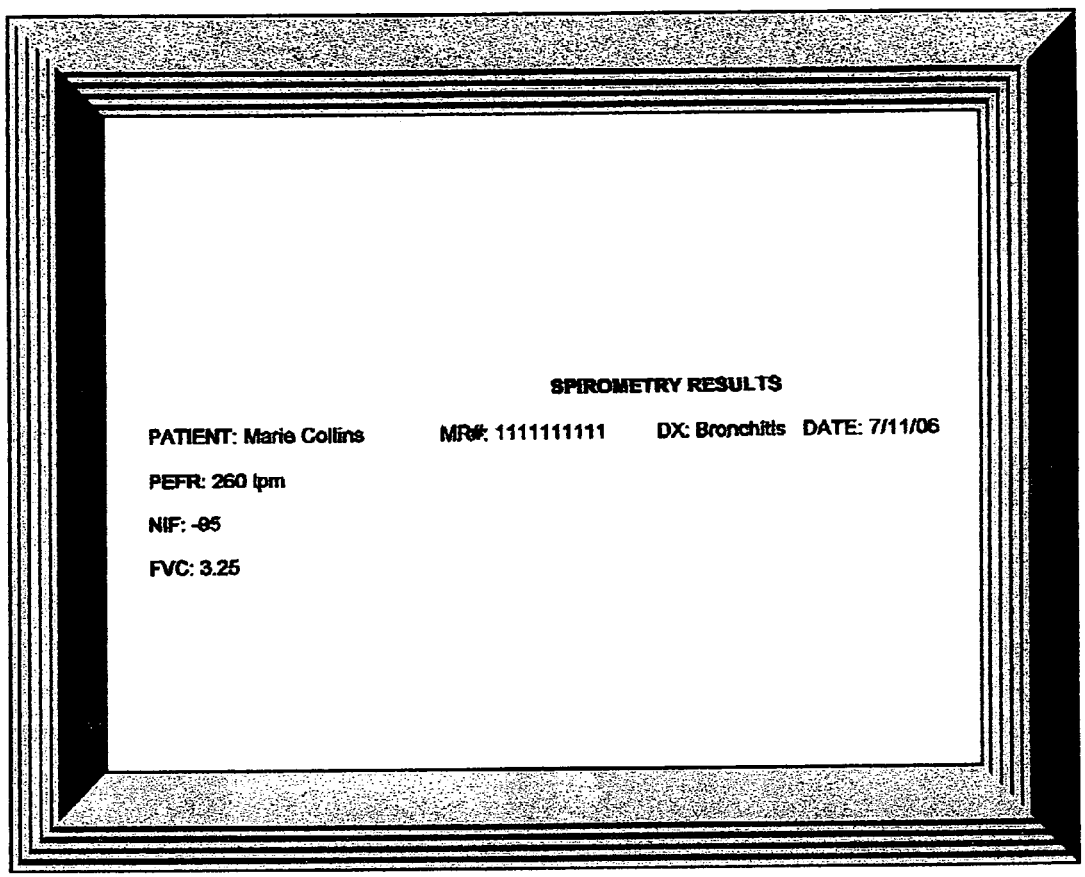
FIG. 16 is an exemplary illustration of a frame of patient information available for display re: spirometry results entered into the hospital archive by a respiratory therapist who performed the test using the mobile respiratory therapy medication dispensing device of the present invention.

FIG. 16 is an exemplary illustration of patient respiratory information that can be displayed on screen 16A when the therapist uses a spirometer to obtain information about a patient's condition before, during or after dispensing medication.

Other embodiments of the present invention comprise the addition of point-of-care arterial blood gas analysis technology. This equipment would significantly diminish the time between initiation of an arterial blood gas order and the delivery of results.

Another embodiment of the present invention comprises the addition of bedside spirometry technology. A spirometer built into the cart would significantly decrease the amount of time between initiation of a physician order and the delivery of the results.

The embodiments outlined above would maximize the respiratory therapist's availability on the patient-care floor, increasing productivity, effectiveness and positively influencing patient outcomes.

Another embodiment of the present invention comprises the addition of a compressed gas source for ease in administration of inhaled pulmonary medications in areas where gasses are not traditionally available or when for example, compressed air is desired instead of oxygen.

The present invention fills a void in the field of respiratory therapy medication dispensation by providing a computerized, mobile unit equipped with a plurality of storage compartments uniquely suited for securely and safely storing and dispensing respiratory therapy medications to patients in an expedited manner. The present invention is capable of significantly reducing costs and errors associated with medication dispensation and improve the security and accuracy of same. Use of the respiratory therapy medication system provided reduces the time that respiratory therapists must devote to medication administration and allows valuable time for the therapists to perform functions of patient care, as appropriate to the scope of a therapist's practice.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A respiratory therapy medication dispensing cart consisting of:

a housing for a respiratory therapy medication dispensing cart that is approximately 35.56 centimeters (cm) (14 inches) wide by approximately 30.48 cm (12 inches) deep by approximately 127.0 cm (50 inches) in height, wherein the height is measured from the bottom of a plurality of swivel wheels to the outer edge of a recessed area supporting a wireless laptop computer and the plurality of swivel wheels includes six wheels for stabilizing the housing and making the housing mobile;

a plurality of different size storage compartments in the housing for storing respiratory therapy medications and supplies including, (i) a wire basket positioned directly underneath the housing between the housing and the plurality of wheels, vertical columns along each perimeter corner of the basket between the housing and the plurality of the wheels, the basket having a width and depth identical to the width and depth of the housing, the basket having four side faces and a closed bottom, each of the side faces having a lower closed sidewall with an upper edge, and an upper open side so that each of the side faces allows for access to an inside of the basket, each side face being between two of the columns, each open side for allowing access to the inside of the basket, each of the side faces having cross brace members that criss-cross each side face of the basket, each cross member having ends that are attached to an upper end portion of each vertical column above each upper edge of each lower closed sidewall and are attached to a lower end portion of each vertical column below each upper edge of each lower closed sidewall, each cross brace having an intersection point where the braces cross one another that is lower than the upper edge of the lower closed sidewall of the basket so as to not obstruct most of the upper open sides of the basket, each of the cross brace members forming structural support for the housing, and the basket stores items selected from the group consisting of nebulizers, aerosol masks, oxygen administration devices, flowmeters and arterial blood gas kits, (ii) a first arrangement of drawers each of the drawers having a width substantially equal to a depth of the drawers and a height approximately one-half the width, the first arrangement of drawers adapted to securely store respiratory therapy supplies selected from the group consisting of prescribed metered dose inhalers (MDIs), unit doses of saline, metered dose inhaler (MDI) spacers, turbohalers, disc inhalers and peak-flow meters, and (iii) a second arrangement of drawers wherein each drawer in the second arrangement of drawers is smaller than the drawers in the first arrangement of drawers, the second arrangement of drawers adapted to securely store patient inhaled pulmonary medications selected from the group consisting of bronchodilators, corticosteroids, inhaled antibiotics and mucolytics;

a plurality of respiratory sensors including at least one of a pulse oximeter, a spirometer and an arterial blood gas analyzer attached to the housing for sensing respiratory conditions of patients in real time;

a central processing unit in the housing for recording respiratory sensed parameters selected from the group consisting of respiratory rates, oxygen levels in the blood, heart rate, lung sounds, respiratory distress, amount and consistency of sputum production, skin color, temperature and diaphoretic condition of a patient in real time;

a staff identification scanning device to avoid unauthorized use of the dispensing cart; and a rechargeable energy source adjacent to the housing for providing power to the sensors and the central processing unit thereby providing a mobile respiratory therapy medication dispensing cart to expedite patient treatment and care.

2. The respiratory therapy cart of claim 1, wherein the respiratory sensor is a pulse oximeter.

3. The respiratory therapy cart of claim 1, wherein the central processing unit for recording is a wireless laptop computer adapted to be operated by a respiratory therapist.

4. The respiratory therapy cart of claim 1, wherein the rechargeable energy source is a battery pack that is electrically recharged.

5. A method for treating patients requiring respiratory therapy using a mobile respiratory therapy medication dispensing cart comprising the steps of:

providing a mobile medication cart that is approximately 35.56 centimeters (cm) (14 inches) wide by approximately 30.48 cm (12 inches) deep by approximately 127.0 cm (50 inches) in height, wherein the height is measured from the bottom of a plurality of swivel wheels to the outer edge of a recessed area supporting a wireless laptop computer having a central processing unit (CPU) with a plurality of respiratory sensors including at least one of a pulse oximeter, a spirometer and an arterial blood gas analyzer, biometric access validation scanner to avoid unauthorized use of the dispensing cart, and respiratory therapy medication dispensers in a plurality of different size storage compartments including, (i) a wire basket positioned directly underneath the housing between the housing and the plurality of wheels, vertical columns along each perimeter corner of the basket between the housing and the plurality of the wheels, the basket having a width and depth identical to the width and depth of the housing, the basket having four side faces and a closed bottom, each of the side faces having a lower closed sidewall with an upper edge, and an upper open side so that each of the side faces allows for access to an inside of the basket, each side face being between two of the columns, each open side for allowing access to the inside of the basket, each of the side faces having cross brace members that criss-cross each side face of the basket, each cross member having ends that are attached to an upper end portion of each vertical column above each upper edge of each lower closed sidewall and are attached to a lower end portion of each vertical column below each upper edge of each lower closed sidewall, each cross brace having an intersection point where the braces cross one another that is lower than the upper edge of the lower closed sidewall of the basket so as to not obstruct most of the upper open sides of the basket, each of the cross brace members forming structural support for the housing, and the basket stores items selected from the group consisting of nebulizers, aerosol masks, oxygen administration devices, flowmeters and arterial blood gas kits, (ii) a first arrangement of drawers each of the drawers having a width substantially equal to a depth of the drawers and a height approximately one-half the width, the first arrangement of drawers adapted to securely store respiratory therapy supplies selected from the group consisting of prescribed metered dose inhalers (MDIs), unit doses of saline, metered dose inhaler (MDI) spacers, turbohalers, disc inhalers and peak-flow meters, and (iii) a second arrangement of drawers wherein each drawer in the second arrangement of drawers is smaller than the drawers in the first arrangement of drawers, the second arrangement of drawers adapted to securely store patient inhaled pulmonary medications selected from the group consisting of bronchodilators, corticosteroids, inhaled antibiotics and mucolytics;

scanning biometric information of a respiratory therapist with the validation scanner in order to access the CPU and the respiratory therapy medication and allow for the cart to be become mobile;

wheeling the mobile cart having six wheels for stabilizing the unit to a patient's bed after validation of the respiratory therapist biometric information;

sensing respiratory conditions of the patient with the respiratory sensors;

entering the sensed respiratory conditions of the patient into the central processing unit;

dispensing respiratory therapy medications from the cart based on the sensed respiratory conditions;

entering the medications dispensed to patient into the central processing unit;

recharging the energy source; and returning the cart for restocking and stocking of respiratory therapy medication.

6. The method of claim 5, wherein the scanning step includes the step of:

scanning the biometric information from a magnetic identification (ID) badge on the respiratory therapist with a magnetic scanner, wherein the validation automatically activates power on the cart and non-validation deactivates the power to the cart.

7. The method of claim 6, wherein the sensing of respiratory conditions includes the step of:

sensing the respiratory conditions by at least one of built-in respiratory equipment, hand-held equipment and manual input by the respiratory therapist.

8. The method of claim 7, wherein the built-in respiratory equipment is a pulse oximeter.

9. The method of claim 5, wherein the entering of respiratory conditions of the patient includes respiratory rate, oxygen levels in the blood, heart rate, lung sounds, work of breathing, amount and consistency of sputum production, skin color, temperature and diaphoretic condition.

10. The method of claim 5, wherein the dispensing of medication includes the step of:
dispensing an inhaled pulmonary medication.

11. The method of claim 10, wherein the inhaled pulmonary medication is at least one of a fast-acting bronchodilator, a less-fast acting bronchodilator, a corticosteroid, an inhaled antibiotic, and a mucolytic.

12. The method of claim 5, wherein the step of entering medication dispensed to patient is based on the sensed conditions by the respiratory therapist and manual in-put thereof.

13. A respiratory therapy medication dispensing cart consisting of:
a housing for a respiratory therapy medication dispensing cart with a height, width and depth wherein the height is measured from the bottom of a plurality of swivel wheels and is approximately 3.5 times the width;
a plurality of swivel wheels includes six wheels for stabilizing the unit and making the housing mobile;
a plurality of different size storage compartments in the housing for storing respiratory patient medications and supplies including,
(i) a wire basket positioned directly underneath the housing between the housing and the plurality of wheels, vertical columns along each perimeter corner of the basket between the housing and the plurality of the wheels, the basket having a width and depth identical to the width and depth of the housing, the basket having four side faces and a closed bottom, each of the side faces having a lower closed sidewall with an upper edge, and an upper open side so that each of the side faces allows for access to an inside of the basket, each side face being between two of the columns, each open side for allowing access to the inside of the basket, each of the side faces having cross brace members that criss-cross each side face of the basket, each cross member having ends that are attached to an upper end portion of each vertical column above each upper edge of each lower closed sidewall and are attached to a lower end portion of each vertical column below each upper edge of each lower closed sidewall, each cross brace having an intersection point where the braces cross one another that is lower than the upper edge of the lower closed sidewall of the basket so as to not obstruct most of the upper open sides of the basket, each of the cross brace members forming structural support for the housing, and the basket stores items selected from the group consisting of nebulizers, aerosol masks, oxygen administration devices, flowmeters and arterial blood gas kits,
(ii) a first arrangement of drawers each of the drawers having a width substantially equal to a depth of the drawers and a height approximately one-half the width, the first arrangement of drawers adapted to securely store respiratory therapy supplies selected from the group consisting of prescribed metered dose inhalers (MDIs), unit doses of saline, metered dose inhaler (MDI) spacers, turbohalers, disc inhalers and peak-flow meters, and
(iii) a second arrangement of drawers wherein each drawer in the second arrangement of drawers is smaller than the drawers in the first arrangement of drawers, the second arrangement of drawers adapted to securely store patient inhaled pulmonary medications selected from the group consisting of bronchodilators, corticosteroids, inhaled antibiotics and mucolytics;
an angled receptacle on the upper right side of cart to hold small devices selected from the group consisting of oxygen nipples, connectors and adaptors;
a hook protruding from the top of the cart for hanging treatment bags and equipment so that the therapist's hands are free;
a plurality of respiratory sensors including at least one of a pulse oximeter, a spirometer and an arterial blood gas analyzer attached to the housing for sensing respiratory conditions of patients in real time;
a central processing unit in the housing for recording respiratory sensed parameters selected from the group consisting of respiratory rates, oxygen levels in the blood, heart rate, lung sounds, respiratory distress, amount and consistency of sputum production, ski color, temperature and diaphoretic condition of a patient in real time;
a staff identification scanning device to avoid unauthorized use of the dispensing cart; and
a rechargeable energy source adjacent to the housing for providing power to the sensors and the central processing unit thereby providing a mobile respiratory therapy medication dispensing cart to expedite patient treatment and care after positive therapist identification, positive patient identification, medication verification at the patient's bedside, while respiratory data are being monitored and recorded in real time.

* * * * *